United States Patent
During (10) Patent No.: US 6,503,887 B1
(45) Date of Patent: Jan. 7, 2003

(54) PERORAL GENE THERAPY OF DIABETES AND OBESITY

(75) Inventor: Matthew J. During, Philadelphia, PA (US)

(73) Assignee: Matthew During, Philadelphia, PA (US)

(*) Notice: Subject to any disclaimer, the term of this patent is extended or adjusted under 35 U.S.C. 154(b) by 0 days.

(21) Appl. No.: 09/510,144

(22) Filed: Feb. 22, 2000

Related U.S. Application Data (60) Provisional application No. 60/120,975, filed on Feb. 19, 1999.

(51) Int. Cl.⁷ .................... A61K 48/00; C12N 15/63; C12N 15/85; C12N 15/87
(52) U.S. Cl. .................... 514/44; 435/320.1; 435/325; 435/455
(58) Field of Search .................... 514/44; 435/320.1, 435/69.1, 455, 325; 424/69.1, 93.1

(56) References Cited

U.S. PATENT DOCUMENTS

| | | | |
|---|---|---|---|
| 5,837,693 A | 11/1998 | German et al. | 514/44 |
| 5,885,971 A | 3/1999 | German et al. | 514/44 |
| 6,004,944 A | 12/1999 | Rothman et al. | 514/44 |
| 6,194,176 B1 * | 2/2001 | Newgard et al. | 435/69.4 |
| 6,258,789 B1 * | 7/2001 | German et al. | 514/44 |

FOREIGN PATENT DOCUMENTS

| | | | |
|---|---|---|---|
| FR | 2 732 978 | 10/1996 | C12N/7/01 |
| WO | WO 96/40269 | 12/1996 | A61K/48/00 |
| WO | WO 98/11779 | 3/1998 | A01N/43/04 |

OTHER PUBLICATIONS

Crystal. Science 1995; 270:404–410.*
Eck et al. Phar Basis Ther 1995; 77–101.*
Freeman et al. Intl J Mol Med 1999; 4:585–592.*
Gros et al. Hum Gene Ther Dec. 1997; 8:2249–59.*
Levine et al. Mol Med Today Apr. 1999; 5:165–171.*
Lodish et al. Mol Cell Bio, W.H. Freeman and Co., 1999, 64–66.*
Mitanchez (Endocrine Rev 1997; 18:520–40.*
Robbins et al, Pharmacol Ther 1998;80:35–47.*
Suiyama et al. Horm. Metab Res Dec. 1997; 29:599–603.*
Verma et al. Nat. Sep. 1997; 389:239–242.*
Miller et al. Hum Gene Ther 1997;8:803–815.*
Leibiger, B. et al., "Expression of Exogenous DNA in Rat Liver Cells After Liposome–mediated Transfection in Vivo," *Biochemical and Biophysical Research Communications*, vol. 174, No. 3, 1223–31 (Feb. 14, 1991).
Sugiyama, A. et al., "Defective Adenoassociated Viral–Mediated Transfection of Insulin Gene by Direct Injection into Liver Parenchyma Decreases Blood Glucose of Diabetic Mice," *Horm. Metab. Res.*, vol. 29, 599–603 (1997).

(List continued on next page.)

Primary Examiner—James Ketter
Assistant Examiner—Q. Janice Li
(74) Attorney, Agent, or Firm—Nutter, McClennen & Fish, LLP; Thomas J. Engellenner; Jasbir Sagoo

(57) ABSTRACT

The invention provide methods and compositions for targeting endocrine cells capable of converting an immature expressed protein into a mature protein, and secreting the expressed protein into the systemic circulation. In particular, the invention features methods and compositions for treating disorders, such as diabetes by orally administering a vector expressing insulin to target cells which can subsequently secrete the expressed insulin into the blood circulation.

39 Claims, 5 Drawing Sheets

OTHER PUBLICATIONS

Zhu, N. et al., "Systemic Gene Expression After Intravenous DNA Delivery into Adult Mice," *Science*, vol. 261, 209–11 (Jul. 9, 1993).

Peng, L. et al., "Construction of Recombinant Adeno–Associated Virus Vector Containing the Rat Preproinsulin II Gene" *J. Surg. Res.* vol. 69 No. 1: 193–198 (Apr. 1997).

Sugiyama, A. et al., "Defective Adeno–Associated Viral–Mediated Transfection of Insulin Gene by Direct Injection into Liver Parenchyma Decreases Blood Glucose of Diabetic Mice" *Horm. Metab. Res.* vol., 29 No. 12: 599–603 (Dec. 1997).

Tanaka, S. et al., "Transfer and Expression of Insulin Gene in Intestinal Cells. Possibility of Oral Delivery Using Defective Herpes Simplex Viral Vector" Database ChemAbs, Database Accession No. 127:75846 HCA XP002147296 141–149 (1996).

* cited by examiner

PERORAL GENE THERAPY OF DIABETES AND OBESITY

CROSS-REFERENCE TO RELATED APPLICATIONS

The present invention claims priority to U.S. Provisional Application No. 60/120,975, filed Feb. 19, 1999 entitled: Peroral Gene Therapy of Diabetes and Obesity.

BACKGROUND OF THE INVENTION

The present invention is generally in the field of methods and compositions for treating metabolic disorders, particularly diabetes and obesity.

Insulin Dependent Diabetes Mellitus (IDDM) is a common condition that results in both high morbidity and high mortality despite the general availability of insulin and the awareness that intensive insulin therapy can maintain euglycemia and significantly reduce complications. The major limitation is that the maintenance of euglycemia requires a regimental approach to monitoring blood glucose, and appropriately administering and tailoring the doses of insulin. Although the use of insulin, has revolutionized the treatment of diabetes, the need for repeated injections, continuous monitoring followed by appropriate dose changes, leads to poor patient compliance and lack of adequate 24 hour control.

Alternative treatments for diabetes include islet cell transplantation, however, this approach has limitations. Specifically, the transplantation requires some invasive surgical intervention and necessitates an immunosuppressant therapy. Moreover, the results from islet cell transplantation have generally been disappointing. Other methods involve ex vivo gene therapy of host cells which may avoid the immune rejection. With ex vivo gene therapy, cells are extracted from an individual and subjected to genetic manipulation by inserting genetic material into the cells. The genetically manipulated cells are implanted back into the individual from which they were removed. The genetic material is then expression in vivo. Although this approach has resulted in successful in vivo expression of the protein, this approach also has limitations, for example, the genetically engineered cells may either be targeted by the underlying autoimmune disease, or undergo uncontrolled cell division and thereby induce tumor growth.

Gene transfer for the treatment of diabetes has been demonstrated using cationic liposome:DNA complexes as described by Leibiger et al. (1991) *Biochem. Biophys. Res. Comm.* 174: 1223–1231. Other studies have shown systemic gene expression after intravenous injection of an expression plasmid:cationic liposome complex (Zhu et al., (1993) *Science* 261, 209–211). However, the results demonstrate poor efficiency of transfection, and a reduction in expression over time. Sugiyama et al. generated an adeno-associated virus (AAV) vector expressing rat insulin (Sugiyama et al. (1997) *Horm. & Metab. Res.* 29, 599–603). These authors demonstrated insulin expression in primary hepatocytes in vitro and then further showed that the vector could be introduced in vivo by direct injection into the liver of diabetic mice. The results of the study showed a mild drop in plasma glucose at 5 days. However, the results demonstrated a transient efficacy reflected by the low titer of vector stocks ($<10^7$/ml), as well as instances of hepatic injury following direct intraparenchymal injection, and low transduction efficiency.

Therefore, a need exists for an in vivo gene therapy approach whereby the target cell is transduced and provides long term, regulatable expression of a target protein.

SUMMARY OF THE INVENTION

The invention provides methods and compositions for targeting endocrine cells capable of converting an immature expressed protein into a mature protein, and secreting the expressed protein into the systemic circulation. The invention is based, in part, on the discovery that endocrine cells, in particular the cells of the diffuse neuroendocine system (DNES), can be modified to incorporate a nucleic acid molecule which expresses a protein with a desired therapeutic effect on a subject. The invention features targeting endocrine cells capable of converting an immature expressed protein into a mature protein.

In particular, the invention features methods and compositions for treating disorders, such as diabetes and obesity by modifying endocrine cells to incorporate a nucleic acid molecule which expresses a desired protein. The expressed protein can be secreted into the systemic circulation to obtain therapeutic blood levels of the protein thereby treating the subject in need of the protein. The transformed endocrine cells provide long term therapeutic effects for disorders associated with a deficiency or misregulation of a particular protein.

In one aspect of the invention, an orally administered vector expressing insulin can be used to target cells which can subsequently secrete the expressed insulin into the blood circulation. More specifically, targeting secretory cells that are capable of converting immature proteins to mature proteins, such as specific cells of the intestine, e.g., DNES cells. The DNES cells are capable of processing pro-insulin into mature insulin by virtue of these cells expressing enzymes that are capable of converting pro-insulin to insulin, e.g., the enzyme, convertase. The insulin is then released into the portal circulation and is able to lower blood glucose.

The invention provides a direct in vivo gene therapy approach that has several advantages over both transplantation and ex vivo gene transfer techniques. Specifically, in vivo somatic cell gene transfer can be used to directly introduce the human insulin gene into host cells without disrupting normal anatomy and without the need for surgical intervention, or the need for immunosuppression to prevent rejection. A continuous low level of endogenous insulin may contribute to an improvement in glycemic control and can delay the onset or slow the progression of diabetic complications. In addition, the subject with diabetes would be protected from ketoacidosis.

Accordingly, the invention features a method for inducing expression of a protein in a specific tissue comprising:
  identifying a tissue that is capable of enzymatically converting an immature protein into a mature protein, and is also capable of secreting the mature protein from the cells into the systemic circulatory system;
  orally administering to the tissue a viral vector comprising a tissue specific promoter and a nucleic acid encoding a protein of interest;
  expressing the protein of interest in the tissue such that if the expressed protein is an immature protein, the tissue enzymatically converts the immature protein into a mature protein prior to secreting the mature protein from the cells into the systemic circulatory system.

In one embodiment, the specific tissue is an endocrine tissue, for example, the intestinal lining and endocrine tissue comprising the diffuse neuroendocine system (DNES) cells. The protein of interest can be selected based on the disorder that requires treatment. If the disorder is diabetes, the protein of interest is insulin or pro-insulin.

In one embodiment, the viral vector is selected from the group consisting of an adeno-associated vector, a parvovirus vector, an adenovirus vector, a herpes virus vector and a lentivirus vector. In a preferred embodiment, the viral vector is an adeno-associated vector.

In another embodiment, the tissue specific promoter is selected from the group consisting of insulin promoter, glucokinase promoter, L-pyruvate kinase promoter, glucagon promoter, elongation factor 1 alpha promoter, and the rat insulin promoter. In a preferred embodiment, the tissue specific promoter is the elongation factor 1 alpha promoter. In another preferred embodiment, the tissue specific promoter is the rat insulin promoter.

In another aspect, the invention features a method for delivering a protein of interest to the systemic circulatory system of a subject comprising:

orally administering a nucleic acid construct into an endocrine tissue in vivo, wherein the nucleic acid construct comprises a nucleotide sequence encoding a protein of interest operably linked to a promoter specific for the endocrine tissue; and expressing the protein of interest in the endocrine tissue such that if the expressed protein is an immature protein, the endocrine tissue comprises at least one enzyme capable of enzymatically converting the immature protein into a mature protein, and wherein the endocrine tissue secretes the mature protein into the systemic circulatory system, to thereby deliver a protein of interest into the systemic circulatory system.

In a preferred embodiment, the step of orally administering the nucleic acid construct comprises administering the nucleic acid construct into the intestine.

In another aspect, the invention features a method for treating diabetes comprising:

orally administering a nucleic acid construct into DNES cells in vivo, wherein the nucleic acid construct comprises a nucleotide sequence encoding insulin operably linked to a promoter specific DNES cells;

expressing a therapeutically effective amount of biologically active insulin in the DNES cells; and secreting the expressed insulin into the systemic circulatory system, to thereby treat diabetes.

In another aspect, the invention features a method for treating diabetes comprising:

orally administering a nucleic acid construct into DNES cells in vivo, wherein the nucleic acid construct comprises a nucleotide sequence encoding pro-insulin operably linked to a promoter specific DNES cells;

expressing a therapeutically effective amount of biologically active pro-insulin in the DNES cells;

converting the pro-insulin to insulin in the DNES cells; and secreting the insulin into the systemic circulatory system, to thereby treat diabetes.

In one embodiment, the insulin is expressed in the DNES cells for at least 3 months. In another embodiment, the insulin is expressed in the DNES cells for at least 6 months. In another preferred embodiment, the DNES cells convert the pro-insulin to insulin using the convertase enzyme.

In another aspect, the invention features a method for regulating blood glucose levels in a subject comprising:

orally administering a nucleic acid construct into DNES cells in vivo, wherein the nucleic acid construct comprises a nucleotide sequence encoding insulin operably linked to a glucose responsive promoter;

expressing a therapeutically effective amount of biologically active insulin in the DNES cells; and secreting the expressed insulin into the systemic circulatory system in an amount sufficient to regulate blood glucose levels.

In one embodiment, the glucose responsive promoter is selected from the group consisting of insulin promoter, glucokinase promoter, L-pyruvate kinase promoter, glucagon promoter, and the rat insulin promoter. In another embodiment, the blood glucose levels are reduced to normal blood glucose levels. In yet another embodiment, the insulin is secreted in response to high blood glucose levels.

In another aspect, the invention features a AAV viral vector for expression of a insulin in the DNES cells comprising a tissue specific promoter and a nucleic acid encoding the insulin.

In a preferred embodiment, the promoter is an insulin promoter.

BRIEF DESCRIPTION OF DRAWINGS

The invention will be more fully understood from the following detailed description taken in conjunction with the accompanying drawings, in which.

The invention will be more fully understood from the following detailed description taken in conjunction with the accompanying drawings, in which.

DETAILED DESCRIPTION OF THE INVENTION

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

So that the invention is more clearly understood, the following terms are defined:

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "systemic circulatory system" or "systemic circulation" as used herein refers to the art known use of the term. The systemic circulatory system serves to transport blood through the body. The systemic circulatory system can be used to elicit an immune response using an antigen that results in the production of antibodies against the antigen. These antibodies continue to exist and circulate throughout the body.

The term "portal circulation" as used herein refers to the art recognized use of the term referring to the circulation in the a large portal vein that carries blood from the stomach and intestines to the liver.

The term "endocrine cells" as used herein refers to a cells capable of secreting a protein expressed therein into the surrounding environment. Examples of endocrine cells are secretory cells that include, but are not limited to DNES cells, vascular smooth muscle, skeletal smooth muscle, cardiac myocytes, anterior pituitary cells, adenohypophyseal cells, L cells, K cells and neurosecretory cells.

The term "regulatory sequence" is art-recognized and intended to include control elements such as promoters, enhancers and other expression control elements (e.g., polyadenylation signals), transcription termination sequences, upstream regulatory domains, origins of replication, internal ribosome entry sites ("IRES"), enhancers, enhancer sequences, post-regulatory sequences, e.g., the woodchuck hepatitis B post-regulatory element (WPRE), and the like, which collectively provide for the replication, transcription and translation of a coding sequence in a recipient cell. Not all of these regulatory sequences need always be present so long as the selected coding sequence is capable of being replicated, transcribed and translated in an appropriate host cell. Such regulatory sequences are known to those skilled in the art and are described in Goeddel, *Gene Expression Technology: Methods in Enzymology* 185, Academic Press, San Diego, Calif. (1990). It should be understood that the design of the viral vector may depend on such factors as the choice of the host cell to be transfected and/or the amount of protein to be expressed.

The term "promoter" is used herein refers to the art recognized use of the term of a nucleotide region comprising a regulatory sequence, wherein the regulatory sequence is derived from a gene which is capable of binding RNA polymerase and initiating transcription of a downstream (3'-direction) coding sequence.

The term "operably linked" as used herein refers to an arrangement of elements wherein the components are configured so as to perform their usual function. Thus, control elements operably linked to a coding sequence are capable of effecting the expression of the coding sequence. The control elements need not be contiguous with the coding sequence, so long as they function to direct the expression of the coding sequence.

For example, intervening untranslated yet transcribed can be present between a promoter sequence and the coding sequence and the promoter sequence can still be considered "operably linked" to the coding sequence.

The term "nucleic acid of interest" as used herein refers to any DNA or RNA molecule which encodes a polypeptide or other molecule which is desirable for administration to a mammalian subject for expression of the product encoded by the nucleic acid of interest and delivery of the encoded product into the blood stream of the mammalian subject. The nucleic acid is generally operatively linked to other sequences which are needed for its expression such as a promoter.

The term "construct" as used herein refers a nucleic acid molecule which contains the nucleic acid of interest, generally operably linked to a promoter for expression of the polypeptide encoded by the nucleic acid of interest. "Constructs" as used herein is generally meant to refer a nucleic acid molecule that facilitates expression of a polypeptide encoded by the nucleic acid to be introduced into a secretory gland cell.

The term "euglycemia" or a "euglycemic state" as used herein refers to a state associated with a level of blood glucose that is normal or nearly normal, particularly relative to the levels of blood glucose in a subject having a disease or condition associated with hyperglycemia. In humans, euglycemia correlates with blood glucose levels in the range of 70 mg/dl to 130 mg/dl.

The invention is described in more detail in the following subsections:

I. Cells and Regulation of Insulin Secretion

The invention provides methods and compositions for gene therapy for disorders such as diabetes, by introducing the nucleic acid encoding insulin into endocrine cells. The human insulin gene encodes pro-insulin which must be processed into insulin for full bioactivity. Pro-insulin, when administered intravenously, has only 8% of the activity of mature insulin on glucose uptake and metabolism in man (Bergenstal et al. (1984) *J. Clin. Endocrinol. Metabol.* 58: 973–979). The conversion of pro-insulin to insulin occurs efficiently in pancreatic β cells and other neuroendocrine cells (Seidah & Chretien, 1997). Processing of pro-insulin to insulin is carried out by the prohormone convertases PC1/PC3 and PC2, which are unique Kex2 family endopeptidases produced primarily in endocrine cells (Seidah & Chrietien, 1997).

Accordingly, the invention provides methods and compositions for gene therapy for disorders such as diabetes, by introducing the nucleic acid encoding insulin into endocrine cells, in particular, cells which resemble the pancreatic β cell. The proteins expressed in pancreatic β cells can respond to glucose levels. Examples of such proteins include, but are not limited to, the GLUT-2 transporter, glucokinase, and ATP-sensitive potassium channels. Suitable cells for gene therapy are those that increase glucose metabolism in response to an increase in extracellular glucose, and possess a secretory apparatus which will translate this increase in extracellular glucose into insulin secretion by the cell.

Examples of suitable cells in addition to pancreatic β cells include, but are not limited to, DNES cells, vascular smooth muscle, skeletal smooth muscle, cardiac myocytes, anterior pituitary cells, adenohypophyseal cells, L cells, K cells and neurosecretory cells. The neurosecretory cells, i.e., neurons, pancreatic β cells and adenohypophyseal cells, particularly somatotrophs, secrete and/or release hormones or transmitters. Adenohypophysea cells are suitable cells because they have pharmacological and biophysical properties that are similar to pancreatic β cells (Bernardi et al. (1993) supra).

Other cells include L and K cells which have a similar glucose sensing and peptide releasing apparatus as pancreatic β cells. L cells of the distal ileum and proximal colon, which under neurohumoral signals from the gut release, neuropeptides, glucagon-like-peptide 1 (GLP-1),glucagon-like-peptide 2 (GLP-2), and glucagon-like-peptide amide. Plasma GLP-1 concentrations increase twofold within 10–15 minutes after intake of a mixed meal (Orskov et al, (1996) *Scandinavian J. Gastroenterology* 31, 665–670). Recent studies have shown that although gastric inhibitory peptide (GIP) is likely to be the critical incretin, both GIP and GLP-1 secretion increase significantly in response to three meals in normal subjects (Orskov et al. (1996) supra). These studies also showed that insulin secretion increased in a corresponding manner to the increase in these neuropeptides. The release of these endogenous neuropeptides from L-cells may be used to stimulate the secretion of ectopically expressed insulin from these cells.

In a preferred embodiment, the cells are of the diffuse neuroendocrine system. The DNES cells express the gut hormones, gastrin, cholecystokimin (CCK), gastric inhibitory peptide (GIP) and glucagon-like peptides (GLP), and following ingestion of food these peptides are secreted into the portal circulation (Orskov et al., (1996) supra; Limb et al., (1997) *Pediatric Res.* 41, 364–367; Ensinck & D'Alessio, (1992) *New Engl. J. Med.* 326, 1352–1353). The DNES cells also express glucokinase and ATP sensitive potassium channels (Mangel et al., (1994) *Peptides* 15, 1565–1566). Moreover, the DNES cells are capable of processing pro-insulin to insulin and can respond appropriately to orally-administered carbohydrate.

Gastrin, CCK and GIP are the hormones released early in the postprandial phase. Gastrin is released primarily in response to amino acids and peptides, in the gut, and CCK release is induced by mixed meals of fat and protein. GIP arises from scattered K cells in the epithelium of the villi and upper crypts of the duodenal and jejunal mucosa, and is released primarily in response to glucose and lipids. In vivo GIP acts as an "incretin" enhancing the secretion of insulin following a carbohydrate intake (Limb et al., (1997) supra).

Insulin produced in the endocrine cells can be secreted into the systemic circulation. Preferably, the insulin is secreted along with the products of digestion, into the portal circulation.

In another embodiment, the insulin is expressed in non-endocrine cells which include, but are not limited to, fibroblasts, hepatocytes and epithelial cells that express furin, a distinct Kex2 family endopeptidase (Fuller et al. (1989) *Science* 246: 482–486). The processing of pro-insulin to insulin is carried out by the prohormone convertases PC1/PC3 and PC2, which are unique Kex2 family endopeptidases with expression limited to endocrine cells (Seidah et al. (1997) *Curr. Opin. Biotech.* 8: 602–607). Non-endocrine cells including that express furin can be used. Furin has a specific consensus sequence that is recognized by the prohormone for its cleavage. Human pro-insulin does not contain this consensus sequence and therefore expression of pro-insulin in non-PCI/PC3, non-PC2 expressing cells, which express furin, will not process pro-insulin efficiently. In one embodiment, a human pro-insulin DNA construct containing genetically engineered furin endoprotease cleavage sites between the B-chain and C-peptide, and between the C-peptide and A-chain, is used. The altered cleavage sites enables the insulin to be processed by the ubiquitous endoprotease furin.

The invention also provides methods and compositions for regulated release of insulin in endocrine cells and non-endocrine cells by using vectors comprising promoters that function in specific endocrine cells. Introducing a nucleic acid encoding insulin into non-endocrine cells typically leads to pro-insulin production and release. Although pro-insulin is capable of effecting glucose uptake and metabolism, it has a lower affinity than insulin for the insulin receptors and a 12-fold lower potency for glucose metabolism. The release of pro-insulin from non-endocrine cells provides a low basal unregulated control of blood glucose concentration. The control of blood glucose concentrations can be enhanced in a regulated manner by the insulin expressed and secreted by the endocrine cells. The invention therefore provides a method of regulating glucose concentrations using both non-endocrine cells and endocrine cells. The non-endocrine cells release pro-insulin with slow stable release kinetics, while the endocrine cells express pro-insulin which is converted to insulin and secrete the insulin into the systemic circulation to provide a dual regulation method for controlling blood glucose concentrations.

The invention also provides methods and compositions for regulated release of insulin in secretory cells by using vectors comprising promoters that function in specific secretory cells. In one embodiment, the regulation of insulin release is directed by promoters capable of expressing insulin in cells and tissues that include, but are not limited to, intestinal tissue, pancreatic β cells, DNES cells, vascular smooth muscle, skeletal smooth muscle, cardiac myocytes, anterior pituitary cells, adenohypophyseal cells, and neurosecretory cells. Suitable promoters include, but are not limited to, the insulin promoter, the glucokinase promoter, the L-pyruvate kinase promoter and the glucagon promoter. Other suitable promoters include the elongation factor 1 alpha promoter and the rat insulin promoter.

In another embodiment, the regulated release of insulin is obtained by transcriptional control of the nucleic acid encoding insulin using regulatory elements which are responsive to glucose. There are a number of genes that are upregulated with feeding or glucose administration, including glucokinase (Liang et al. (1994) *Diabetes* 43: 1138–1145) and the L-isoform of pyruvate kinase, LPK (Ogier et al. (1987) *Eur. J. Biochem.* 166: 365–370; Cuif et al. (1997) *FEBS Letters* 417: 81–84) and insulin itself (Goodison et al. (1992) *Biochem. J.* 285: 563–568 and Melloul et al. (1993) *Proc. Natl. Acad. Sci.* 90: 3865–3869). Regulatory elements derived from such genes, e.g., glucokinase and LPK, are suitable for regulating gene expression. For example, regulatory elements such as promoters, that switch on expression of the insulin gene when extracellular glucose levels are higher than normal. The transcriptional regulation of the nucleic acid encoding insulin may be obtained by using feeding and/or glucose-responsive promoters that regulate insulin production and release.

To test the effect of regulatory elements and their effect on glucose, the in vitro STC-1 model can be used. The STC-1 cell-line is derived from transgenic mice where a "leaky" insulin promoter is operably linked to the SV40 T antigen and comprises the same genes as those expressed in intestinal STC-1 cells. This STC-1 cell-line also expresses GIP and provides a suitable model for in vitro vector characterization (Kieffer et al. (1995) *Am. J. Physiol.* 269: E316–322).

II H Vectors and Delivery Systems

The vectors for delivery of the nucleic acid of interest can be either viral, non-viral, or naked DNA. In one embodiment, the vector is a viral vector, such as recombinant adeno-associated virus (AAV). The viral vector is selected based on the nucleic acid molecule to be delivered, the cell to be targeted, and the disorder to be treated. For example, in diabetes the insulin gene is the primary gene, although the glucose transporter, glucokinase, prohormone convertases, amylin and ATP-sensitive potassium channel are additional genes which might be considered. In a preferred embodiment, the human pro-insulin (hIns) gene is used for the production of human insulin. The DNA for hIns is about 5 kb in length and can be readily packaged into an AAV particle.

AAV vectors can be constructed using known techniques to provide operatively linked components of control elements including a transcriptional initiation region, a nucleotide sequence encoding a protein of interest, and a transcriptional termination region. The control elements are selected to be functional in the targeted cell. The resulting construct which contains the operatively linked components can be flanked at the 5' and 3' region with functional AAV ITR sequences.

The preferred AAV is AAV-2 as described by Kotin et al. (1994) *Human Gene Therapy* 5:793–801; Berns "Parvoviridae and their Replication" in Fundamental Virology, 2nd Edition, (B. N. Fields and D. M. Knipe, eds.), although other AAV serotypes can be used in the invention. Examples of other AAV serotypes include, but not limited to, AAV-1, AAV-2, AAV-3, AAV-4, AAV-5, AAVX7, and the like.

Control sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) *Cell 41:521–530*, herpesvirus thymidine kinase (HSV-TK) promoter (McKnight et al. (1984) *Cell* 37: 253–262), β-actin MO promoters (e.g., the human β-actin promoter as described by Ng et al. (1985) *Mol. Cell Biol.* 5: 2720–2732) and colony stimulating factor-1 (CSF-1) promoter (Ladner et al. (1987) *EMBO J*. 6: 2693–2698). Alternatively, tissue-specific regulatory elements can be used, such as tissue specific promoters.

Promoters can be used to obtain regulation by targeting specific cells which retain regulated release to food and carbohydrate consumption, e.g. L and K cells of the gut. In a preferred embodiment, a promoter element responsive to ambient glucose levels is used. The preferred promoter is the insulin promoter itself. Alternative promoters include the L-pyruvate kinase promoter, the glucagon promoter, and the glucokinase promoters.

Post-transcriptional regulatory elements (PRE) can be used to increase the production of the expressed protein. PRE sequences are commonly found in viruses which replicate via reverse transcription, particularly viruses whose protein products are translated from unspliced transcripts. These sequences regulate the transport of the unspliced viral transcripts from the cell nucleus to the cytoplasm where they are expressed. Examples of viruses for which PRE sequences have been identified include retroviruses, such as human and feline immunodeficiency virus (HIV and FIV) (See e.g., Cullen et al. (1991) *J. Virol.* 65: 1053; and Cullen et al. (1991) *Cell* 58: 423–426), and hepatitis B virus, e.g., the woodchuck post-transcriptional regulatory element. (See e.g., Huang et al. (1995) *Molec. and Cell Biol.* 15: 3864–3869; Huang et al. (1994) *J. Virol.* 68: 3193–3199, Huang et al. (1993) *Molec. and Cell. Biol.* 13: 7476–7486).

In order to produce AAV particles, an AAV vector is introduced into a suitable host cell using known techniques, such as by transfection. A number of transfection techniques are generally known in the art. See, e.g., Graham et al. (1973) *Virology*, 52:456, Sambrook et al. (1989) Molecular Cloning, a laboratory manual, Cold Spring Harbor Laboratories, N.Y., Davis et al. (1986) Basic Methods in Molecular Biology, Elsevier, and Chu et al. (1981) *Gene* 13:197. Particularly suitable transfection methods include calcium phosphate co-precipitation (Graham et al. (1973) *Virol.* 52:456–467), direct micro-injection into cultured cells (Capecchi (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transduction (Felgner et al. (1987) *Proc. Natl. Acad. Sci. USA* 84:7413–7417), and nucleic acid delivery using high-velocity microprojectiles (Klein et al. (1987) *Nature* 327:70–73).

Suitable host cells for producing AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO dhfr-cells (Urlaub and Chasin (1980) *Proc. Natl. Acad. Sci. USA* 77:4216–4220), 293 cells (Graham et al. (1977) *J. Gen. Virol.* 36: 59) or myeloma cells like SP2 or NS0 (Galfre and Milstein (1981) *Meth. Enzymol.* 73(B):3–46).

In one embodiment, cells from the stable human cell line, 293 (readily available through, e.g., the ATCC under Accession No. ATCC CRL1573) are preferred in the practice of the present invention. Particularly, the human cell line 293, which is a human embryonic kidney cell line that has been transformed with adenovirus type-5 DNA fragments (Graham et al. (1997) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce AAV particles.

Host cells containing the AAV vectors are preferably rendered capable of providing AAV helper functions in order to replicate and encapsidate the exogenous nucleic acid molecule flanked by the AAV ITRs to produce AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

The term "AAV rep coding region" as used herein refers to the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. For a description of the AAV rep coding region, see, e.g., Muzyczka (1992) *Current Topics in Microbiol. and Immunol.* 158:97–129; and Kotin (1994) *Human Gene Therapy* 5:793–801. Suitable homologues of the AAV rep coding region include the human herpesvirus 6 (HHV-6) rep gene which is also known to mediate AAV-2 DNA replication (Thomson et al. (1994) *Virology* 204:304–311).

The term "AAV cap coding region" as used herein refers to the art-recognized region of the AAV genome which encodes the capsid proteins VP1, VP2, and VP3, or functional homologues thereof. These cap expression products supply the packaging functions which are collectively required for packaging the viral genome. For a description of the AAV cap coding region, See, e.g., Muzyczka (Supra). AAV helper functions can be introduced into the host cell by transfecting the host cell with an AAV helper construct either prior to, or concurrently with, the transfection of the AAV vector, AAV helper constructs are thus used to provide at least transient expression of AAV rep and/or cap genes to complement missing AAV functions that are necessary for productive AAV infection. AAV helper constructs lack AAV ITRs and can neither replicate nor package themselves.

These helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. (See, e.g., Samulski et al. (1989) *J. Virol.* 63:3822–3828; and McCarty et al. (1991) *J. Virol.* 65:2936–2945). A number of other vectors have been described which encode Rep and/or Cap expression products. See, e.g., U.S. Pat. No. 5,139,941.

As a consequence of the infection of the host cell with a helper virus, the AAV Rep and/or Cap proteins are produced. The Rep proteins also serve to duplicate the AAV genome. The expressed Cap proteins assemble into capsids, and the recombinant AAV genome is packaged into the capsids. This results in AAV replication, and the DNA is packaged into AAV particles. Following recombinant AAV replication, AAV partilces can be purified from the host cell using a variety of conventional purification methods, such as CsCl gradients. The resulting AAV particles are then ready for use for DNA delivery to various cell types.

In another embodiment, the vector of the invention can be a virus other than the adeno-associated virus, which allows for expression of a nucleic acid molecule introduced into the viral nucleic acid. For example, replication defective retroviruses, adenoviruses and lentivirus can be used. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. The genome of adenovirus can be manipulated such that it encodes and expresses the protein of interest but is inactivated in terms of its ability to replicate in a normal lytic viral life cycle. See e.g., Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art.

Delivery systems include methods of in vitro, in vivo and ex vivo delivery of the vector. Generally, the vector can be delivered to the gut by oral administration, preferably using an orogastric, thus eliminating the problems of invasive access by either intraportal venous injection, or transplantation of genetically altered cells, or direct intraparencymal injection. For in vivo delivery, the vector can be administered to a subject in a pharmaceutically acceptable carrier. The term "pharmaceutically acceptable carrier", as used herein, refers to any physiologically acceptable carrier for in vivo administration of the vectors of the present invention. Such carriers do not induce an immune response harmful to the individual receiving the composition, and are discussed in section III. In one embodiment, the vector can be distributed locally to a specific site, for example, the intestinal tissue and DNES cells. In a preferred embodiment, the vector is delivered perorally into the gut using an orogastric tube.

In another embodiment, the nucleic acid encoding the desired protein, e.g., insulin, can be delivered using a non-viral delivery system. This includes delivery of the nucleic acid encoding the desired protein to a target tissue in colloidal dispersion systems that include, for example, macromolecule complexes, nanocapsules, microspheres, beads, and lipid-based systems including oil-in-water emulsions, micelles, mixed micelles, and liposomes.

For example, gene transfer for diabetes has been demonstrated using cationic liposome:DNA complexes. Leibiger et al. (1991) directly introduced genes into hepatocytes in vivo using liposome encapsulated DNA (See Leibiger et al. (1991) supra). Other studies have shown systemic gene expression after intravenous injection of an expression plasmid:cationic liposome complex (Zhu et al., (1993) *Science* 261, 209–211).

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) *Biotechniques*, 6:682). Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3β-[N-(N', N' dimethylaminoethane) carbamoyl] cholesterol.

In one embodiment, particle-mediated delivery using a gene-gun can be used as a method to introduce the nucleic acid of interest to a target cell. Suitable particles for gene gun-based delivery of include gold particles which are coated with the nucleic acid of interest. In one embodiment, the nucleic acid of interest can be delivered as naked DNA without an expression vector. In another embodiment, the DNA encoding the protein of interest can be inserted into an expression plasmid. Gene gun based delivery are described, for example by, Braun et al. (1999) *Virology* 265:46–56; Drew et al. (1999) *Vaccine* 18:692–702; Degano et al. (1999) *Vaccine* 18:623–632; and Robinson (1999) *Int J Mol Med* 4:549–555; Lai et al. (1998) *Crit Rev Immunol* 18:449–84;See e.g., Accede et al. (1991) *Nature* 332: 815–818; and Wolff et al. (1990) *Science* 247:1465–1468 Murashatsu et al., (1998) *Int. J. Mol. Med.* 1: 55–62; Agracetus et al. (1996) *J. Biotechnol.* 26: 37–42; Johnson et al. (1993) *Genet. Eng.* 15: 225–236).

III Pharmaceutical Compositions and Pharmaceutical Administration

The vectors of the invention can be incorporated into pharmaceutical compositions suitable for administration to a subject. Typically, the pharmaceutical composition comprises the vector of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. In one embodiment, the mode of administration is parenteral (e.g., intravenous, subcutaneous, intraperitoneal, intramuscular). In another embodiment, the mode of administration is by intravenous infusion or injection. In another embodiment, the mode of administration is by intramuscular or subcutaneous injection. In the most preferred embodiment, the mode of administration is oral e.g., using an orogastric tube.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vectors of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, vectors of the invention can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The vectors of the invention can be used alone or in combination to treat diseases. For example, the vector can be used alone or in combination with an additional agent, e.g., an agent which imparts a beneficial attribute to the therapeutic composition e.g., an agent which effects the viscosity of the composition. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of a vector of the invention. A "therapeutically effective amount" refers to an amount effective, at dosages and for periods of time necessary, to achieve the desired therapeutic result. A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV Uses

A disease or a disorder in which levels of glucose, e.g. high levels of glucose are detrimental is a disorder in which modulation of the glucose concentration is expected to alleviate the symptoms and/or progression of the disorder. Vectors of the invention containing nucleic acid encoding insulin or por-insulin can be introduced and expressed in a subject in an amount suitable to ameliorate, reduce, alleviate or aid in, or at least partially correct the disorder. Alleviation of the disorders may be evidenced, for example, by the reduction of glucose levels in blood or plasma of diabetic mice (See Example 6).

Other disorders that can be treated or modified by the methods and compositions of the invention include obesity. Mouse models for obesity are known in that art, for example, obese-diabetic mice (ob/ob), and obese-diabetic (db/db) mice from the Jackson Laboratories (Bar Harbor, Me). (See e.g., Collins et al. (1996) *J. Biol Chem* 271:9437–9440; Darling (1996) *Curr Opin Genet Dev* 6:289–294; Andersson (1996) *Ann. Med.* 28:5–7; Van Heek et al. (1997) *J. Clin. Invest* 99:385–390). These animal models can be used to assess the effect of an anorexigenic peptide, e.g., leptin on obesity.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

Construction of AAV Cloning Plasmids and pAA Virus

This example describes the construction of AAV vectors comprising the insulin or pro-insulin cDNA. The human pro-insulin cDNA was cloned into the AAV cloning plasmid containing the elongation factor 1 alpha (EF) promoter (2.5 kb fragment) and a polylinker followed by the Woodchuck Hepatitis Post Regulatory Element (WPRE) and a SV40 polyadenylation signal. In a promoter analysis study the EF promoter provided stronger expression than other constitutive promoters and this expression was enhanced approximately 10 fold by use of the WPRE element. The resulting expression cassette, referred to as the pAAV-EF-hIns-WPRE plasmid was used to produce AAV viral particles. Other constructs were also generated using specific promoters, such as the rat insulin promoter (RIP) and the human pro-insulin cDNA constructs containing genetically engineered furin endoprotease cleavage sites between the B-chain and C-peptide, and between the C-peptide and A-chain. These furin constructs were constructed using the EF promoter and the RIP promoter and are referred to as pAA-VEF-fur-hIns and pAAV-RIP-fur-hIns, respectively.

This pAAV-EF-hIns-WPRE plasmid was packaged to generate high titer rAAVhIns viral particles using a helper plasmid, pDG (gift of Dr. Jurgen Kleinschmidt, Heidelberg). The helper plasmid contains both the rep and cap open reading frames, as well the minimal set of adenoviral genes necessary for helper functions. The vectors were generated using calcium phosphate transfection of both plasmids into 293 cells. Vector stocks wee purified using ammonium sulfate followed by double cesium banding. The bands containing the viral particle were isolated from the cesium chloride preparation and dialysis into suitable buffer.

Particle titers were determined using an ELISA assay kit available (Progen, Inc.) which uses an A20 monoclonal antibody that recognizes intact particles. Typically, concentrations of $10^{13}$ particles were routinely obtained from one standard petridish of 293 cells. The packaging and purification methods are described in detail by Xiao et al. (1998) *J. Virol.* 72: 2224–2232. and During et al., (1998) *Nature Med.* 4:1131–1135) with modifications as described by Grimm et al. (1999) *Hum Gene Ther* 10, 2745–2760).

Example 2

Generation of Streptozotocin (STZ)-treated Diabetic Rats

Diabetes was induced in Wistar male rats, 250–280 grams. The rats were injected intraperitoneally with streptozotocin (STZ) dissolved in 0.9% physiologic saline at a dose of 100 mg/kg body. Rats were kept in individual cages for 4–6 days then reinjected with streptozotocin at same dosage.

Induction of diabetes was confirmed by measuring blood glucose levels of the STZ rats every 3 days using a Beckman glucose Analyzer IL. Rats whose blood glucose levels exceeded 20 mmol/L (>360 mg/dl) were regarded as STZ diabetic rats and used for further study.

Example 3

In vivo Vector Administration

In vivo infection of rats (STZ-induced diabetic rats or control rats) was performed under mild anaesthesia (intraperitoneal injection of a 2:1 ratio, by volume of ketamine 100 mg/ml and xylazine 20 mg/ml at a dose of 1 ml/kg). A 20 g oral feeding tube was passed from the mouth to the stomach of each rat, and the vector administered in 200 microliters of water at $10^9$, $10^{10}$ and $10^{11}$ ELISA units of rAAVhIns. rAAV-EF-fur-hIns was administered in 100 μl and 200 μl of $5 \times 10^{11}$/ml, and pAAV-RIP-fur-hIns at $2 \times 10^{12}$/ml. Rats were fasted for 12 hours prior to procedure and on water only for 24 hours post vector administration. Animals administered saline and AAVlac were used as controls.

Example 4

Tissue Preparation

Rats were sacrificed by overdose of chloral hydrate injected intraperitoneally and perfused with 2% paraformaldehyde in PBS. Tissue samples were stored in 1% formaldehyde, 15% and 30% sucrose successively before being frozen and sectioned (40 micron thickness).

For histological analysis, sections were assessed for insulin expression by immunocytochemistry using specific anti-human insulin and pro-insulin primary antibodies (Chemicon) with immunofluoresence detection (During et al., (1998) supra)

Example 5

Stable Expression of the Insulin Gene in Rat DNES Following Oral Administration of AAV Vectors Following rAAVhIns administration via an orogastric tube, gene expression was determined at multiple time points from 3 hours (n=4), 6 hours (n=12), 3 days (n=15), 1 month (n=4) and 3 months (n=3). Analysis by immunohistochemistry revealed that no expression of insulin was observed at 3 hours, however, robust expression was obtained at 6 hours post infection. Moreover, the expression persisted stably for at least 3 months. The pattern of insulin expression showed successful transduction DNES cells and lamina propria cells, particularly the duodenum and jejunum. Lower levels of expression were observed in the stomach and ileum. With injection of 40 microliters of approximately $10^9$/ml tansducing unit vector stock, greater than 50% of epithelial cells in the proximal stall intestine were transduced and 18% of lamina propria cells by 3 days. This level of expression was persistent at 17–19% at one month and six month timepoints in the lamina propria. The total number of cells transduced was also stable at 8–13 million over this period. These numbers yielded an overall transduction efficiency of 25% in the gut based on the vector dose administered. The vector did not spread beyond the GI system, as determined by RT-PCR analysis of lung, gonads, kidney, heat and brain.

Thus, the oral gene delivery approach produced persistent expression of insulin in luminal intestinal cells. The data also suggests that gene expression may have persisted either within the epithelial cells of the gut or the post-nitotic, terminally differentiated DNES cells, This is because epithelial cells typically turnover every 3–5 days, therefore, for expression to persist in this population of cells, one would have had to transduced the progenitor cell population residing in the Opts. The 6 hour and 3 day animals showed expression in all regions of the villi including some expression in the crypts. At one month, expression in this cell population, in contrast to the maintenance of expression in the lamina propria, had diminished. However, a large number of terminally-differentiated luminal cells, which appear on conceal as DNES cells are stably transduced.

Example 6

Phenotypic Correction of Diabetes in STZ Rats Using rAAVhIns

Diabetic rats were generated using streptozotocin (65 mg/kg i.p.) which was administered once a baseline blood fasting glucose level was attained. Serial blood measurements were taken via tail vein and analyzed for glucose as previously described (During et al., (1995) *J. Clin. Invest.* 95: 2403–2408). On Day 7, rats were administered either AAVlac (control) or AAVhIns at doses of $10^9$, $10^{10}$, and $10^{11}$ virion particles as defined by the Progen ELISA kit. Tail vein blood samples were taken at repeated intervals including Days 3, 7, 14, 56 and 72. This group of animals was maintained for one year before gene expression studies are carried out with PCR and RT-PCR concerning persistence of vector DNA and MRNA expression.

Figure 1:
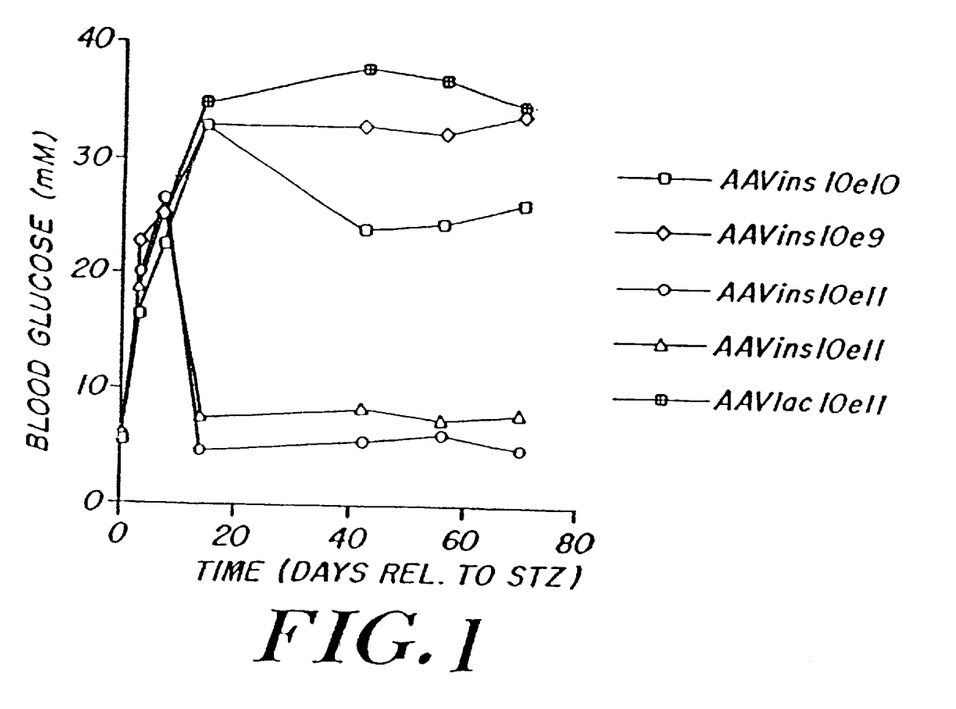
FIG. 1 is a graph showing the blood glucose concentrations following peroral administration of three doses of the AAVIns vector particles at $10^9$, $10^{10}$, and $10^{11}$ (as determined by ELISA) and a control saline treated rat. The rats were delivered systemic streptozotocin (STZ) at Day 0 and the vector was administered on Day 7.

The results of these studies are shown in FIGS. 1–5. The DNES cells are stably transduced. FIG. 1 shows the effect of on insulin expression on blood glucose concentration using rAAVhIns at $10^9$, $10^{10}$ and $10^{11}$ ELISA units from day 0 to day 80 in STZ rats. The data shows the reduction in blood glucose levels with $10^9$ ELISA units of rAAVhIns, and a reduction back to normal with $10^{10}$ and $10^{11}$ ELISA units of rAAVhIns.

Figure 2:
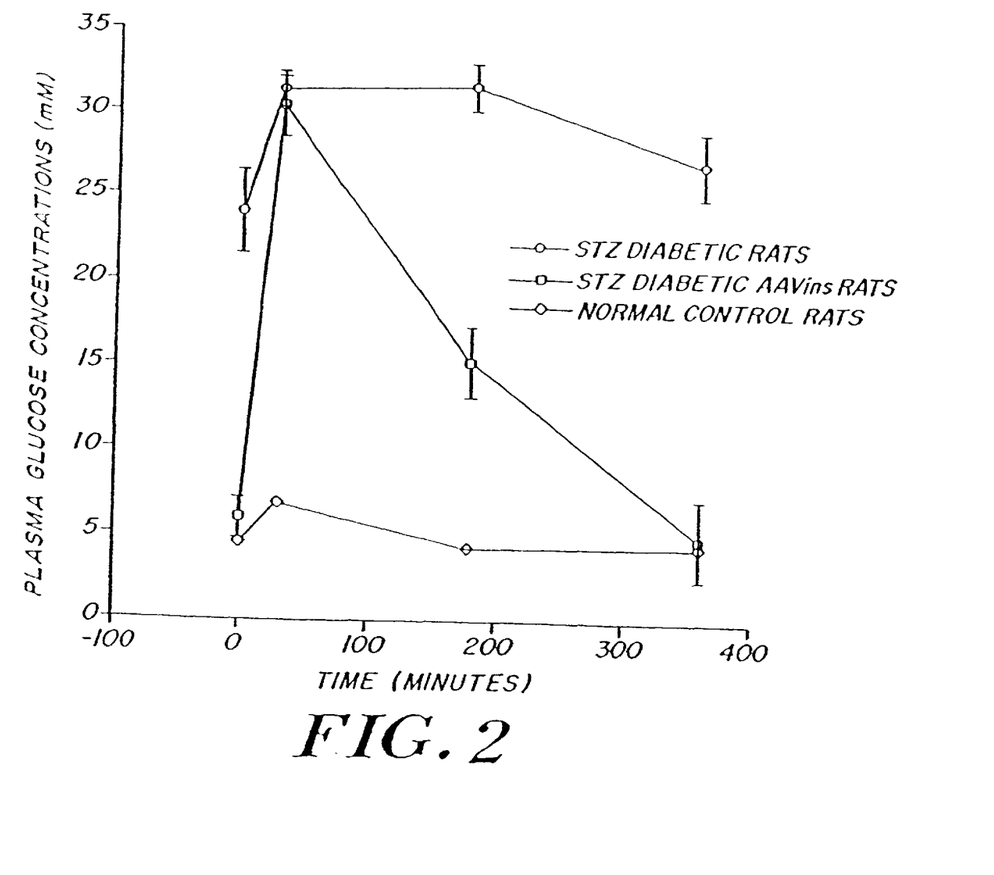
FIG. 2 is a graph showing the plasma glucose concentration in rats treated with STZ (circles), the reduction in plasma glucose concentrations in rats treated with the AAVIns vector (squares), compared to the normal control rats (diamonds)

FIG. 2 shows the plasma glucose levels of rats treated with AAVhIns following an oral glucose challenge. The data shows that glucose levels remain high in STZ diabetic rats not treated with AAVhIns (circles). However, in STZ diabetic rats treated with AAVhIns (squares), the glucose concentration in the blood rapidly decreased and returns to normal baseline concentrations within 6 hours.

Figure 3:
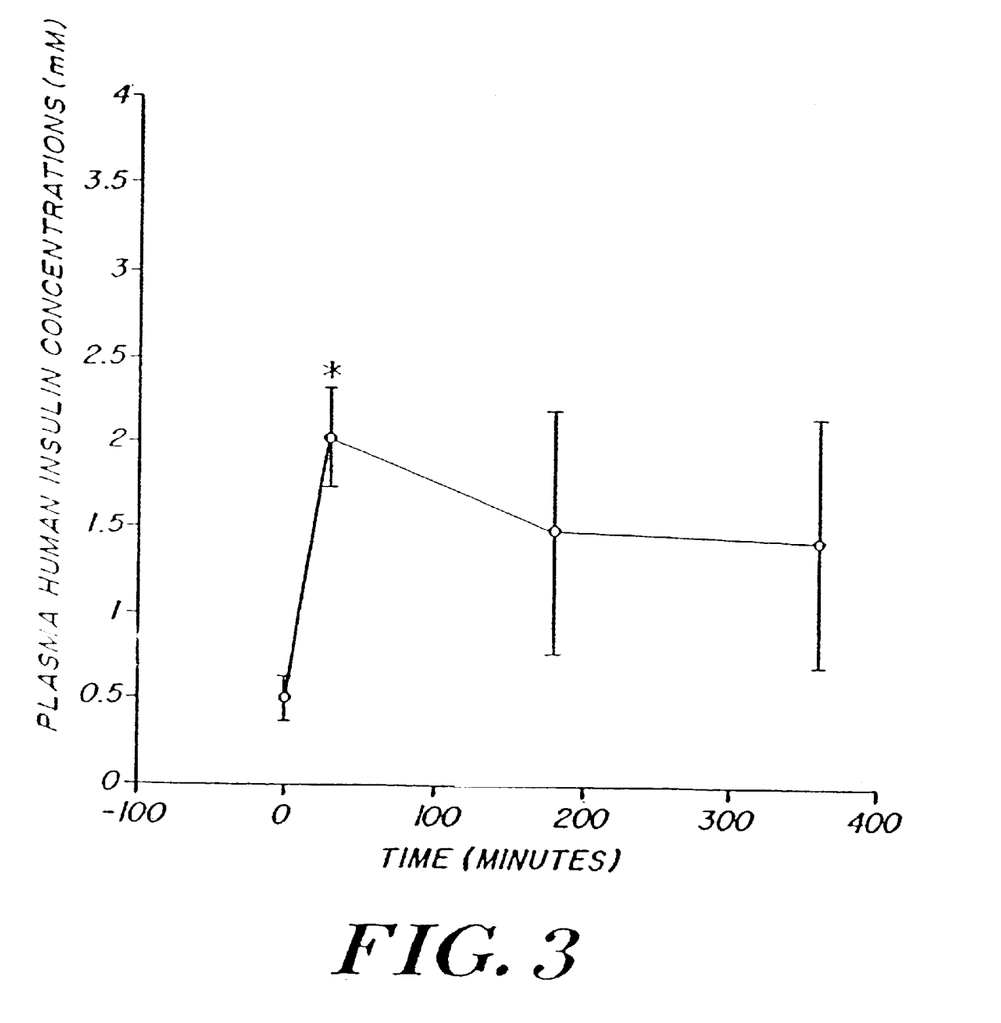
FIG. 3 is a graph showing the plasma human insulin levels in rats treated with the AAVIns vector, demonstrating the regulation of insulin release in the plasma.

Regulation of the insulin produced from AAVhIns is shown in FIG. 3. The data demonstrates a 4 fold increase in insulin production from 0.5 units to 2.0 units in about 20 minutes after the oral glucose challenge, and a steady maintenance of insulin production at about 1.5 units for up to 400 minutes after the challenge, These rats were treated with AAVhIns 3 months before an acute glucose challenge with 1 ml of 20% dextrose solution.

Figure 4:
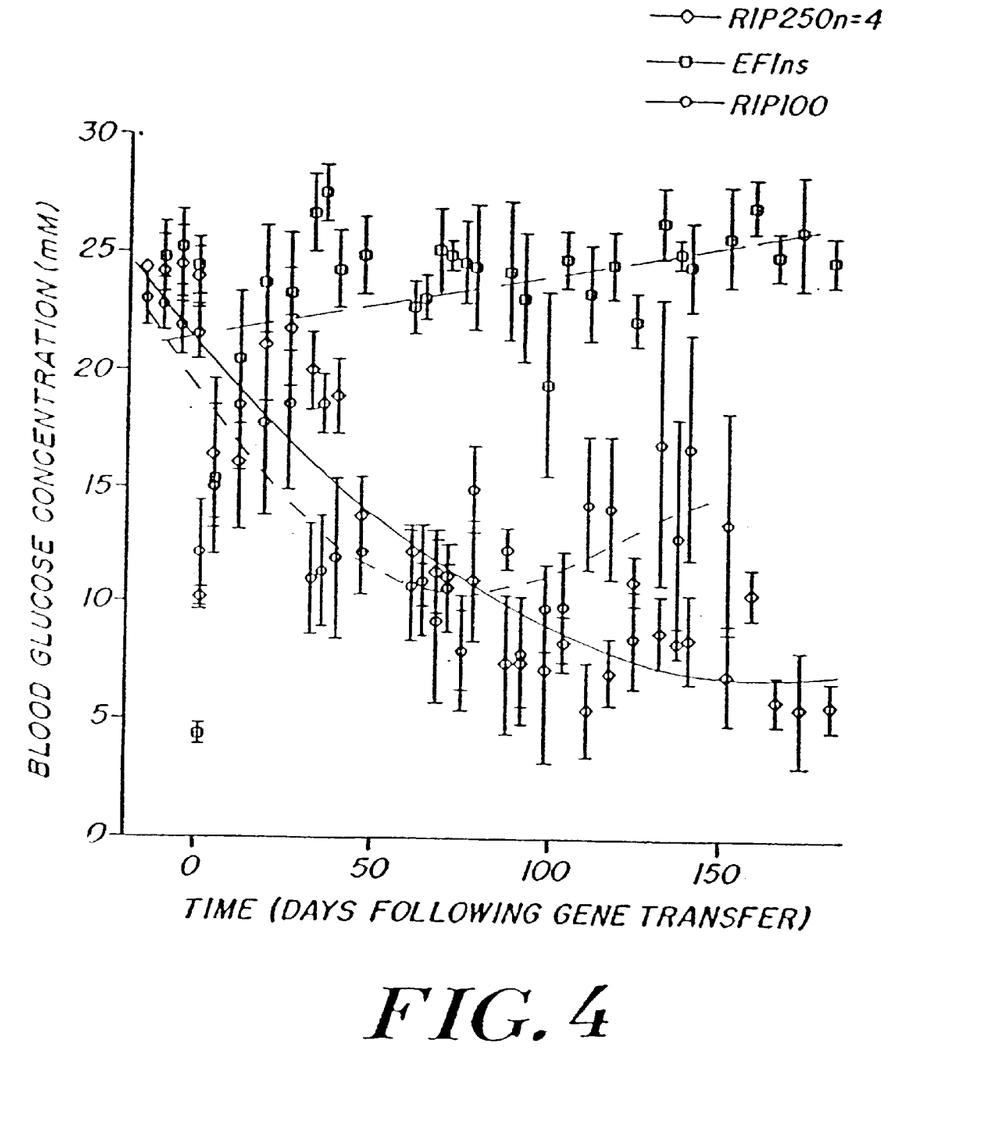
FIG. 4 is a graph showing the effect on blood glucose concentration following peroral administration of AAVIns vectors with either the elongation factor 1 alpha promoter (EF) or the rat insulin promoter (RIP)
Figure 5:
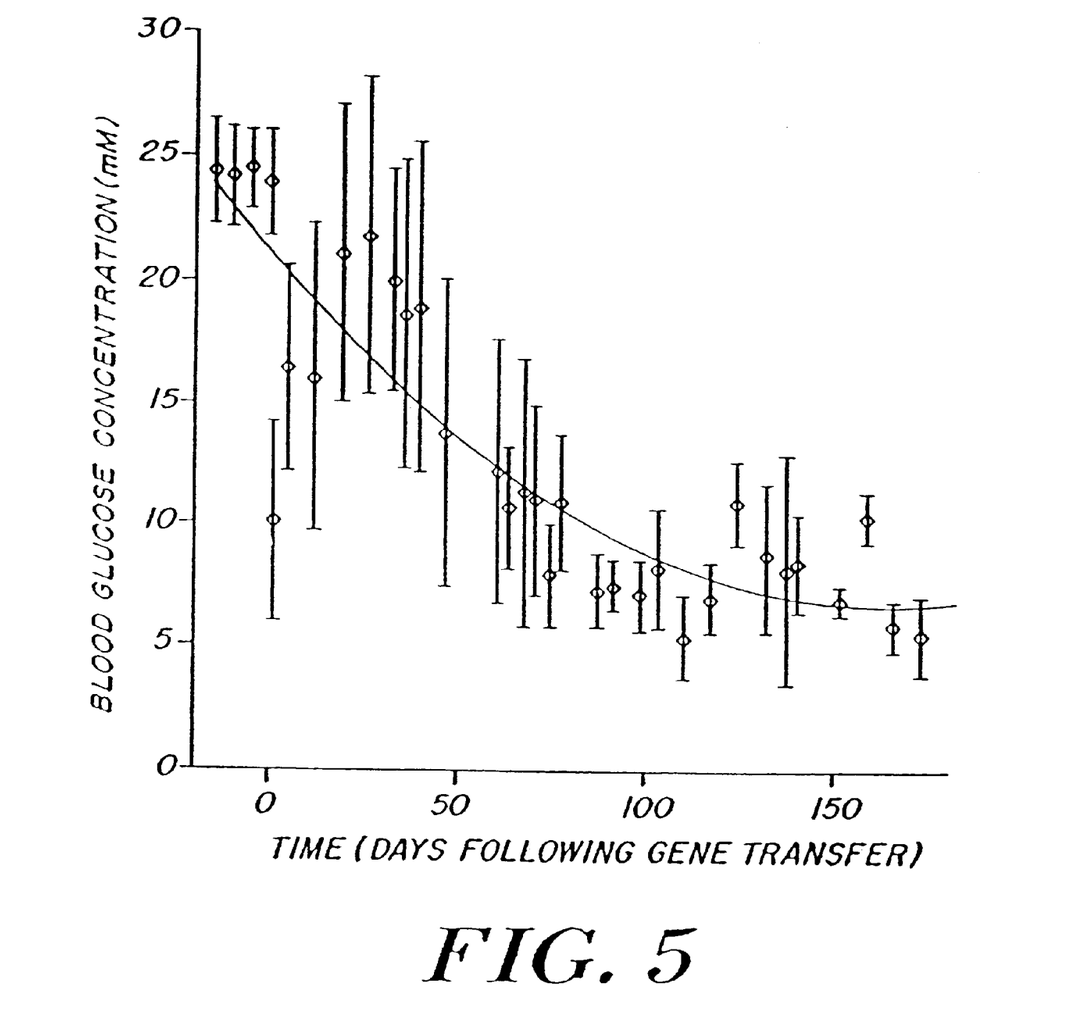
FIG. 5 is a graph showing the effect on blood glucose concentration following peroral administration of AAVfurIns with the rat insulin promoter (RIP).

FIG. 4 shows The effect of different promoters on the production of insulin from the AAVhIns vector. The data shows the more efficient reduction in blood glucose levels using the AAVhIns vector with the RIP promoter at 250 ml (n=4) and 100 ml 100 ml of a $10^{12}$ particle vector stock compared wit the constitutive EF promoter. The data demonstrates that the constitutive EF promoter is more likely to express the insulin epithelial cells rather then the RIP promoter that targets DNES cells. The robust epithelial expression of the EF promoter vector is reflected in the acute (1 day) drop in blood glucose as seen in FIG. 4. As epithelial cells are shed approximately every three days, the reversion to baseline glucose concentrations shows that the vector has most likely been removed with the epithelial cells. In contrast, the RIP promoter function in DNES and continues to express insulin and reduce blood glucose concentrations for at least 180 days after gene transfers. FIG. 5 shows the steady state reduction in blood glucose concentrations using the furin insulin construct with the RIP.

I claim:
1. A method for delivering a protein a gut tissue of a subject comprising:
   targeting gut tissue that is capable of enzymatically converting an immature protein into a mature protein, and is also capable of secret the mature protein from the cells into the systemic circulatory system;
   orally deliver to the gut tissue a viral vector comprising a promoter functional in gut tissue and a nucleic acid encoding a protein of interest wherein the vector expresses the protein of interest in the gut tissue, wherein the expressed protein is an immature protein, and the gut tissue enzymatically converts the immature protein into a mature protein prior to secreting the mature protein from the cells into the systemic circulatory system.

2. The method of claim 1 wherein the gut tissue is an endocrine tissue.

3. The method of claim 2 wherein the endocrine tissue is an intestinal lining.

4. The method of claim 2 wherein the endocrine tissue comprises diffuse neuroendocine system (DNES) cells.

5. The method of claim 1 wherein the protein of interest is pro-insulin.

6. The method of claim 1 wherein the viral vector is selected from the group consisting of an adeno-associated vector, and a parvovirus vector.

7. The method of claim 1 wherein the promoter is selected from the group consisting of insulin promoter, elongation factor 1 alpha promoter, and the rat insulin promoter.

8. The method of claim 1 wherein the promoter is the elongation factor 1 alpha promoter.

9. The method of claim 1 wherein the promoter is the rat insulin promoter.

10. A method for delivering a protein of interest to the systemic circulatory system of a subject comprising:
    orally delivering a nucleic acid construct to an endocrine tissue in vivo, wherein the nucleic acid construct comprises a nucleotide sequence encoding a protein of interest operably linked to a promoter functional in the endocrine tissue; and expressing the protein of interest in the endocrine tissue, wherein the expressed protein is an immature protein, and the endocrine tissue comprises at least one enzyme capable of enzymatically converting the immature protein into a mature protein, and wherein the endocrine tissue secrets the mature protein into the systemic circulatory system, to thereby deliver a protein of interest into the systemic circulatory system.

11. The method of claim 10 wherein the endocrine tissue is the intestinal lining.

12. The method of claim 10 wherein the endocrine tissue comprises diffuse neuroendocine system (DNES) cells.

13. The method of claim 10 wherein the step of orally administering the nucleic acid construct comprises administering the nucleic acid construct into the intestine.

14. The method of claim 10 wherein the protein of interest is pro-insulin.

15. The method of claim 10 wherein the promoter is selected from the group consisting of insulin promoter, elongation factor 1 alpha promoter, and the rat insulin promoter.

16. The method of claim 10 wherein the nucleic acid construct is contained within a viral vector.

17. The method of claim 16 wherein the viral vector is selected from the group consisting of adeno-associated vector and a parvovirus vector.

18. The method of claim 17 wherein the viral vector is an adeno-associated vector.

19. A method for reducing blood glucose levels in a subject comprising:

orally delivering a nucleic acid construct to DNES cells in vivo, wherein the nucleic acid construct comprises a nucleotide sequence encoding pro-insulin operably linked to a promoter specific for DNES cells;

expressing a therapeutically effective amount of biologically active pro-insulin in tho DNES cells;

converting the pro-insulin to insulin in the DNES cells; and secreting the insulin into the systemic circulatory system, to thereby reduce blood glucose levels in a subject.

20. The method of claim 19 wherein the promoter is the elongation factor 1 alpha promoter.

21. The method of claim 19 wherein the promoter is the rat insulin promoter.

22. The method of claim 19 wherein the step of converting the pro-insulin to insulin comprises using the convertase enzyme.

23. The method of claim 19 wherein the insulin is expressed in the DNES cells for at least 6 months.

24. A method for reducing blood glucose levels in a subject comprising:

orally delivering a nucleic acid construct to DNES cells in vivo, wherein the nucleic acid construct comprises a nucleotide sequence encoding pro-insulin operably linked to a glucose responsive promoter;

expressing a therapeutically effective amount of biologically active pro-insulin in We DNES cells;

converting the pro-insulin to insulin in the DNES cells; and secreting the expressed insulin into the systemic circulatory system in an amount sufficient to reduce blood glucose levels.

25. The method of claim 24 wherein the glucose responsive promoter is selected from the group consisting of insulin promoter, elongation factor 1 alpha promoter, and the rat insulin promoter.

26. The method of claim 24 wherein the blood glucose levels are reduced to normal blood glucose levels.

27. The method of claim 24 wherein the insulin is secreted in response to high blood glucose levels.

28. An AAV viral vector for expression of insulin in DNES cells comprising a glucose responsive promoter, a nucleic acid encoding insulin, followed by a woodchuck post-transcriptional regulatory element.

29. The vector of claim 28 wherein the promoter is the insulin promoter.

30. The vector of claim 28 wherein the post-transcriptional regulatory element is the woodchuck hepatitis post-transcriptional regulatory element.

31. A method for delivering a protein in a gut tissue of a subject comprising:

targeting gut tissue that is capable of ethically converting an immature protein into a mature protein, and is also capable of secreting the mature protein from the cells into the systemic circulatory system;

orally delivering to the gut tissue a viral vector comprising a tissue specific promoter functional in gut tissue and a nucleic acid encoding a protein of interest wherein the vector expresses the protein of interest in the gut tissue, wherein the expressed protein is an immature protein, and the gut tissue enzymatically converts the immature protein into a mature protein prior to secreting the mature protein from the cells into the systemic circulatory system.

32. The method of claim 31 wherein the gut tissue is an endocrine tissue.

33. The method of claim 32 wherein the endue tissue is an intestinal lining.

34. The method of claim 32 wherein the endocrine tissue comprises diffuse neuroendocine system (DNES) cells.

35. The method of claim 31 wherein the protein of interest is pro-insulin.

36. The method of claim 31 wherein the viral vector is selected from the group consisting of an adeno-associated vector and a parvovirus vector.

37. The method of claim 31 wherein the promoter is selected from the group consisting of insulin promoter, elongation factor 1 alpha promoter, and the rat insulin promoter.

38. The method of claim 31 wherein the promoter is the elongation factor 1 alpha promoter.

39. The method of claim 31 wherein the promoter is the rat insulin promoter.

* * * * *